United States Patent
Wang et al.

(10) Patent No.: US 12,173,332 B2
(45) Date of Patent: Dec. 24, 2024

(54) MUTANTS OF D-AMINO ACID TRANSAMINASE OBTAINED BASED ON SUPERCOMPUTING-ASSISTED TECHNOLOGY AND APPLICATION THEREOF

(71) Applicant: SHANDONG COMPUTER SCIENCE CENTER (NATIONAL SUPERCOMPUTER CENTER IN JINAN), Shandong (CN)

(72) Inventors: Xin Wang, Jinan (CN); Ming Yang, Jinan (CN); Xiaoming Wu, Jinan (CN); Fuqiang Wang, Jinan (CN); Yan Liang, Jinan (CN); Zhenya Chen, Jinan (CN); Chao Mu, Jinan (CN)

(73) Assignee: SHANDONG COMPUTER SCIENCE CENTER (NATIONAL SUPERCOMPUTER CENTER IN JINAN), Shandong (CN)

(*) Notice: Subject to any disclaimer, the term of this patent is extended or adjusted under 35 U.S.C. 154(b) by 0 days.

(21) Appl. No.: 18/577,824

(22) PCT Filed: Jul. 26, 2023

(86) PCT No.: PCT/CN2023/109243
§ 371 (c)(1),
(2) Date: Jan. 9, 2024

(87) PCT Pub. No.: WO2024/146119
PCT Pub. Date: Jul. 11, 2024

(65) Prior Publication Data
US 2024/0279625 A1    Aug. 22, 2024

(30) Foreign Application Priority Data
Jan. 5, 2023   (CN) .................. 202310009831.4

(51) Int. Cl.
*C12N 9/10* (2006.01)
*G16B 5/00* (2019.01)

(52) U.S. Cl.
CPC .... *C12N 9/1096* (2013.01); *C12Y 206/01021* (2013.01); *G16B 5/00* (2019.02)

(58) Field of Classification Search
None
See application file for complete search history.

(56) References Cited

FOREIGN PATENT DOCUMENTS

| | | |
|---|---|---|
| CN | 105441404 A | 3/2016 |
| CN | 111826362 A | 10/2020 |

(Continued)

OTHER PUBLICATIONS

Mondo et al., GenBank accession No. XP_031942666.1, Mar. 8, 2021.*

(Continued)

*Primary Examiner* — Erin M. Bowers
(74) *Attorney, Agent, or Firm* — Oliff PLC

(57) ABSTRACT

A new mutant of D-amino acid transaminase, based on supercomputing-assisted technology, belongs to the fields of computational biology, computer-aided design, and enzyme engineering technology, and specifically relates to mutants of D-amino acid transaminase obtained based on supercomputing-assisted technology and applications thereof. Compared to the wild-type enzyme, the aforementioned mutant of D-amino acid transaminase exhibits a half-life ($t_{1/2}$) of over 12 hours at 40° C., while it is only 8.8 minutes for the wild-type D-amino acid transaminase. The half-inactivation temperature ($T_{50}^{15}$) of the mutant is 45.3° C., approximately 5.4° C. higher than that of the wild-type D-amino acid transaminase. This substantially enhances its thermal stability, enzymatic activity, etc., effectively broadening its application fields and scope. The mutant has a wide range of (Continued)

industrial applications and thus holds substantial practical value.

8 Claims, 3 Drawing Sheets

(56) References Cited

FOREIGN PATENT DOCUMENTS

| CN | 112359030 A | 2/2021 |
|---|---|---|
| CN | 114134128 A | 3/2022 |
| CN | 114921432 A | 8/2022 |
| CN | 115873819 A | 3/2023 |

OTHER PUBLICATIONS

Mondo et, al. "D-aminoacid aminotransferase-like PLP-dependent enzyme;" GENBANK; 2021; XP_031942666.1.

Nov. 19, 2023 Search Report issued in International Patent Application No. PCT/CN2023/109243.

Nov. 19, 2023 Written Opinion of the International Searching Authority issued in International Patent Application No. PCT/CN2023/109243.

* cited by examiner

MUTANTS OF D-AMINO ACID TRANSAMINASE OBTAINED BASED ON SUPERCOMPUTING-ASSISTED TECHNOLOGY AND APPLICATION THEREOF

The present invention claims priority based on a Chinese patent application filed with the China National Intellectual Property Administration (CNIPA) on Jan. 5, 2023, bearing the application number 202310009831.4 and titled "Mutants of D-amino acid transaminase obtained based on supercomputing-assisted technology and application thereof". The entire contents of the application are incorporated herein by reference for all purposes.

TECHNICAL FIELD

The present invention belongs to the fields of computational biology, computer-aided design and enzyme engineering technology, and specifically relates to mutants of D-amino acid transaminase obtained based on supercomputing-assisted technology and application thereof.

BACKGROUND

Any discussion of the prior art throughout the specification should not be taken as an admission that such prior art is widely known or forms part of the common general knowledge in the art.

With the advancement of computer technology, strategies employing computational techniques to assist protein engineering have gained significant attention, with rational design emerging as a future direction for protein modification.

Specifically, molecular docking, quantum/classical molecular dynamics simulations, quantum mechanics, and quantum chemistry using supercomputing techniques can be used to predictively evaluate the properties of mutants in terms of structure, binding free energy, reaction barriers, and stability. For instance, Aalbers et al. improved the thermal stability of alcohol dehydrogenase ADHA using the FRESCO algorithm while maintaining its activity comparable to the wild-type. In recent years, machine learning has been increasingly applied to protein engineering. It allows for the mining and training of vast protein data sets, thereby aiding in the prediction of protein structures, enhancing properties such as enzyme stability and solubility, and predicting substrate specificity, guiding protein design. In 2018, Nobel Laureate in Chemistry F. H. Arnold successfully enhanced the enantioselectivities of nitric oxide dioxygenase from 76% (S)-ee to 93% (S)-ee and reversed it to 79% (R)-ee through machine learning combined with directed evolution.

Chiral amines are small molecular compounds with a chiral center containing an amine group, playing a crucial role as intermediates in drug synthesis. Recently, with the expanding market for chiral drugs, chiral amines and their derivatives account for 70% of the chiral drug market, including neurologic drugs, cardiovascular medications anti-infective drugs, vaccines, etc. The significant market demand for chiral amine drugs and natural amino acids highlights the importance of efficient chiral amine compound production.

Amino transferases are key enzymes in the biotechnological production of chiral amines, capable of reversibly catalyzing the transfer of amino groups between ketone compounds and amino-containing compounds to synthesize amine compounds. D-amino acid transaminase (D-ATA) from *Aspergillus* pseudonomiae, using pyridoxal phosphate (PLP) as a cofactor, catalyzes the transfer of amino groups from amino compounds to ketone acceptors, producing chiral amines and ketone by-products. The catalytic process is as follows:

Although transaminases show promising application prospects in chiral amine synthesis, the wild-type enzymes still have deficiencies in substrate specificity, stability, catalytic efficiency, etc., hindering their application in large-scale production. Thermodynamic experiments indicate that the half-life of the wild-type D-amino acid transaminase from *Aspergillus* at 40° C. is only 8.8 minutes, necessitating modifications for thermal stability. Enhancing the enzyme's thermal stability would help accelerate reaction rates, increase the solubility of insoluble organic substances, prevent contamination by other microorganisms during the reaction, etc. With the continuous development of supercomputing technology, obtaining thermally stable enzymes through molecular dynamics simulation techniques has become a research focus for efficiently and rapidly customizing robust enzymes.

Molecular dynamics simulation is a method based on the principles of Newtonian mechanics to simulate the physical motion trajectories and states of atoms and molecules. For more complex biomolecular systems, the trajectories of particles within the system are determined by numerically solving Newton's equations of motion for interacting particles, with the interparticle forces and potential energy defined by molecular mechanics force fields. However, due to the geometric growth of computational data, existing molecular dynamics simulation methods based on ordinary computing devices struggle to meet the requirements for rapid and efficient analysis. Simple parallel computing methods using multiple computers consume significant hardware resources and are still limited in computational efficiency. Therefore, researching the preparation methods of biologically active enzymes with enhanced thermal stability assisted by supercomputing is of great significance.

SUMMARY

In response to the problems existing in the current technology, the present invention successfully developed a thermally stabilized mutant of D-amino acid transaminase from *Aspergillus pseudonomiae*, utilizing supercomputing-assisted technology. Based on the above research findings, the present invention was provided.

Specifically, the present invention involves the following technical solutions.

In the first aspect of the present invention, a mutant of D-amino acid transaminase is provided. The mutant of D-amino acid transaminase is obtained by mutations at 16 amino acid sites of a wild-type D-amino acid transaminase, with the following mutations: N23P, E35P, Y36P, V37P, E41P, K88P, V89P, E95P, M189P, A192P, Y199P, V232P, E255P, V288P, Q292P, W301P; wherein, the NCBI accession number of the wild-type D-amino acid transaminase is XP_031942666.1.

The present invention obtains the aforementioned mutant of D-amino acid transaminase based on supercomputing-assisted technology, starting from the wild-type D-amino acid transaminase. Compared to the wild-type D-amino acid transaminase, the aforementioned mutant of D-amino acid transaminase exhibits a half-life ($t_{1/2}$) of over 12 hours at 40° C., significantly longer than the 8.8 minutes of the wild-type (WT). The half-inactivation temperature ($T_{50}^{15}$) of the mutant is 45.3° C., which is approximately 5.4° C. higher than the WT (39.9° C.). This substantially enhances its thermal stability, enzymatic activity and so on, effectively broadening its application fields and scope.

In the second aspect of the present invention, a polynucleotide molecule is provided. The polynucleotide molecule encodes a mutant of D-amino acid transaminase as described in the first aspect of the present invention.

In the third aspect of the present invention, a recombinant expression vector is provided. The recombinant expression vector contains a polynucleotide molecule as mentioned in the second aspect of the present invention.

The recombinant expression vector is obtained by effectively connecting the mentioned polynucleotide molecule with an expression vector, which can be chosen from plasmids. In a specific embodiment of the present invention, the plasmid is pET-28a (+).

In the fourth aspect of the present invention, a host cell is provided. The host cell contains a recombinant expression vector as described in the third aspect of the present invention, or has a polynucleotide molecule as described in the second aspect of the present invention chromosomally integrated, or express a mutant of D-amino acid transaminase as described in the first aspect of the present invention.

The host cell is a prokaryotic cell or a eukaryotic cell.

The host cell is a bacterial cell or a fungal cell.

In a specific embodiment of the present invention, the host cell may be *Escherichia coli* (*E. coli*) or its derivative bacteria, specifically, the host cell is *E. coli* BL21 (DE3).

In the fifth aspect of the present invention, a method for fermenting a mutant of D-amino acid transaminase is provided. The method includes culturing a host cell as described above, and isolating the mutant of D-amino acid transaminase.

In the sixth aspect of the present invention, an application of a mutant of D-amino acid transaminase as described in the first aspect, a polynucleotide molecule as described in the second aspect, a recombinant expression vector as described in the third aspect, a host cell as described in the fourth aspect, and a method as described in the fifth aspect in the field of chiral amine synthesis is provided.

Specifically, the chiral amine synthesis involves converting pyruvate to D-alanine; more specifically, the chiral amine synthesis may be carried out at 40° C.

In the seventh aspect of the present invention, a method for obtaining a mutant of D-amino acid transaminase as mentioned above is provided. The method includes: performing a supercomputing-assisted molecular dynamics simulation of a wild-type D-amino acid transaminase at 40° C. and 50° C. for 20 ns using CHARMM (Chemistry at HARvard Macromolecular Mechanics) force field and GROMACS 5.1.2, analyzing and statistically processing the Root Mean Square Fluctuation (RMSF) from the simulation results; calculating the difference in RMSF values of each amino acid of the wild-type D-amino acid transaminase at 40° C. and 50° C., $\Delta RMSF = RMSF_{50° C.} - RMSF_{40° C.}$; selecting amino acids with a difference greater than 0.5 Å for proline scanning, identifying key amino acid sites affecting thermal stability, and obtaining thermally stabilized mutants of D-amino acid transaminase based on mutation verification and thermal stability testing.

Beneficial Technical Effect of One or More of the Above Technical Solutions

Based on supercomputing-assisted technology, the present invention successfully developed a new mutant of D-amino acid transaminase and applied it effectively. Compared to the wild-type enzyme, the aforementioned mutant of D-amino acid transaminase exhibits a half-life ($t_{1/2}$) of over 12 hours at 40° C., significantly longer than the 8.8 minutes for the wild-type (WT). The half-inactivation temperature ($T_{50}^{15}$) of the mutant is 45.3° C., which is approximately 5.4° C. higher than the WT (39.9° C.). This substantially enhances its thermal stability, enzymatic activity and so on, effectively broadening its application fields and scope. The mutant has a wide range of industrial applications and thus holds substantial practical value.

BRIEF DESCRIPTION OF THE DRAWINGS

The accompanying drawings to the specification, which form part of the present invention, are used to provide a further understanding of the present invention, and the illustrative examples of the present invention and the description thereof are used to explain the present invention and are not unduly limiting the present invention.

DESCRIPTION OF THE PREFERRED EMBODIMENTS

It should be noted that the following detailed descriptions are all illustrative and intended to provide further clarification of the present invention. Unless otherwise indicated, all technical and scientific terms used herein have the same meaning as commonly understood by one of ordinary skill in the art to which the present application belongs.

It is to be noted that the terms used herein are intended only to describe specific embodiments and are not intended to limit the exemplary embodiments according to the present application. As used herein, the singular form is intended to include the plural form as well, unless the context clearly indicates otherwise, and it should also be understood that when the terms "comprising" and/or "including" are used in this specification, they indicate the presence of features, steps, operations, devices, components, and/or combinations thereof. Experimental methods in the following specific embodiments in which specific conditions are not indicated are generally in accordance with the conventional methods and conditions of molecular biology within the art of the field, such techniques and conditions being fully explained in the literature. For example, see the techniques and conditions described in Sambrook et al., *Molecular Cloning: A Laboratory Manual*, or as recommended by the manufacturer.

The present invention is further elucidated with examples below, but these should not be construed as limiting the invention. It should be understood that these examples are provided solely for the purpose of illustration and should not be used to limit the scope of the present invention.

Example 1

Figure 1:
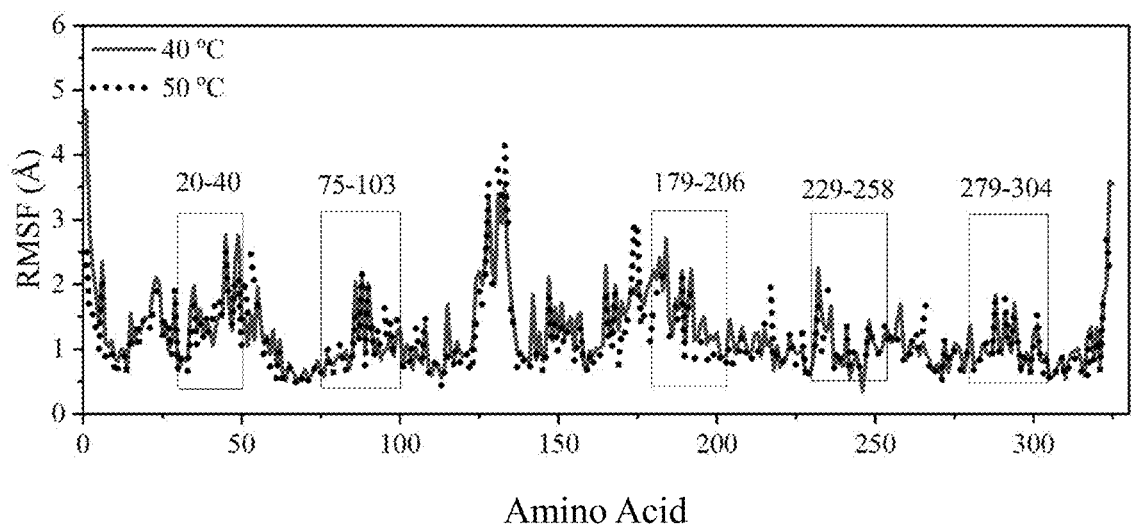
FIG. 1 shows the RMSF analysis of each amino acid in the wild-type D-amino acid transaminase obtained from a 20 ns supercomputing-assisted molecular dynamics simulation at 40° C. and 50° C. in Example 1 of the present invention. The rectangular boxes highlight the regions where ΔRMSF>0.5 Å, indicating regions with concentrated amino acid sites.

A method for obtaining a mutant of D-amino acid transaminase includes conducting 20 ns of supercomputing-assisted molecular dynamics simulations on D-ATA (NCBI accession number XP_031942666.1) at 40° C. and 50° C. using the CHARMM force field and GROMACS 5.1.2, and analyzing and statistically processing the RMSF from the simulation results. RMSF indicates the structural change of an atom over time relative to a reference conformation, reflecting the atom's degree of freedom (flexibility). By calculating the difference in RMSF values of each amino acid at 40° C. and 50° C. ($\Delta RMSF=RMSF_{50° C.}-RMSF_{40° C.}$), amino acids with a difference greater than 0.5 Å were selected for proline scanning to identify key sites affecting thermal stability, the results were shown in FIG. 1. A thermally stabilized mutant, M1, i.e., the aforementioned mutant of D-amino acid transaminase, was obtained through supercomputing-assisted design, mutation verification, and thermal stability testing.

Example 2

(1) Materials and Reagents

D-ATA and its mutant genes were synthesized by Tsingke Biotechnology Co., Ltd. and the plasmid used was pET-28a (+). Isopropyl β-D-1-thiogalactopyranoside (IPTG), kanamycin sulfate, pyridoxal-5'-phosphate (PLP), and the modified Bradford protein concentration determination kit were purchased from Sangon Biotech (Shanghai) Co., Ltd. The Ni-NTA chromatography matrix was purchased from Beijing TransGen Biotechnology Co., Ltd. Dimethyl sulfoxide (DMSO), pyruvate, and (R)-α-methylbenzylamine were purchased from Aladdin Biochemical Technology Co., Ltd.

(2) Expression and Purification of Enzyme

An appropriate amount of *E. coli* BL21(DE3) strains was taken, including the wild-type strain and the mutant strain. These strains were each inoculated into 5 mL of Luria-Bertani (LB) liquid medium containing 50 μg/mL kanamycin sulfate and incubated at 37° C., 200 rpm for 12 hours. The culture was then transferred to 200 mL of LB medium containing 50 μg/mL kanamycin sulfate at 2% inoculation volume (v/v) and continued to incubate at 37° C., 200 rpm for 2-3 hours. When the OD600 reached 0.8, 0.5 mM IPTG was added, and protein expression was induced at 28° C., 200 rpm. After 12 hours of induction, the bacteria were collected by centrifugation at 8000 r/min, 4° C.

The bacterial cells were washed twice with 100 mM PBS buffer (pH 7.5) to remove residual medium and suspended in 50 mL of lysis buffer (50 mM sodium dihydrogen phosphate, 300 mM sodium chloride, 20 mM imidazole, pH 8.0). The cells were homogenized using a homogenizer under ice bath conditions. The cell homogenate was centrifuged at 8000 rpm, 4° C. for 1 hour, and the supernatant containing D-ATA was collected as crude enzyme solution. The crude enzyme solution was then filtered through a 0.45 m filter membrane and subjected to Ni-NTA affinity chromatography column for the separation and purification of the target protein.

Purification Buffers were as Follows:

20 mM imidazole buffer: 50 mM sodium dihydrogen phosphate, 300 mM sodium chloride, 20 mM imidazole, pH 8.0.

50 mM elution buffer: 50 mM sodium dihydrogen phosphate, 300 mM sodium chloride, 50 mM imidazole, pH 8.0.

250 mM elution buffer: 50 mM sodium dihydrogen phosphate, 300 mM sodium chloride, 250 mM imidazole, pH 8.0.

Specific Purification Steps (1) Equilibration of Ni-NTA affinity chromatography column: the column was equilibrated by sequentially washing with 20% (v v) ethanol solution, deionized water, and 20 mM imidazole buffer, each for three column volumes.

(2) Sample Loading: the crude enzyme solution was filtered through a 0.45 m filter membrane using a syringe, and the target protein with six histidine tags was bound to the matrix.

(3) Washing: the column was washed with 20 mM imidazole buffer and 50 mM elution buffer, each for three column volumes. Bradford solution was used to check for the complete removal of impurities.

(4) Elution: elution was performed with 250 mM elution buffer, and 5 mL of the eluate was collected.

Example 3

Protein Concentration Determination

A modified Bradford protein concentration assay kit was used to establish a protein content standard curve and determine the concentration of the purified enzyme. The preparation steps for the protein standard curve were conducted according to the instructions provided with the kit. The molecular weight and purity of the purified protein were identified using the SDS-PAGE method.

Protein concentration determination: the target protein was diluted to fall within the linear range of the BSA standard curve. The absorbance at 595 nm (A595) was measured using a microplate reader, and the protein concentration after dilution was calculated using the linear equation.

Figure 2:
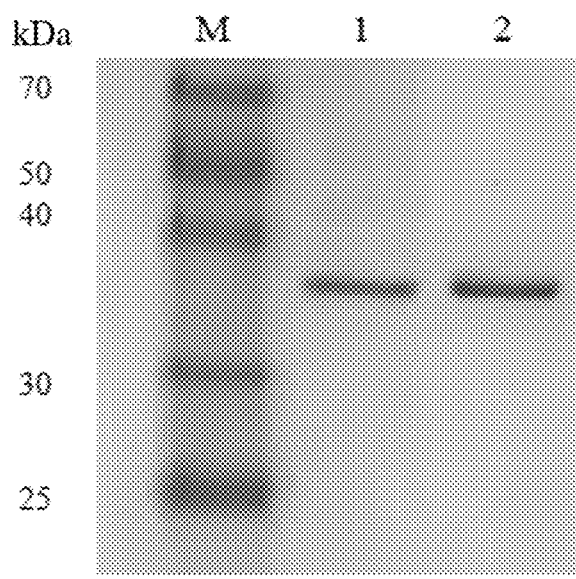
FIG. 2 shows the SDS-PAGE electrophoresis analysis results of the wild-type D-amino acid transaminase and its mutant in Example 3 of the present invention. The lanes are as follows: M: protein marker; lane 1: purified wild-type enzyme solution; lane 2: purified mutant M1 enzyme solution.

The SDS-PAGE electrophoretic profiles of the wild-type and mutant were shown in FIG. 2. The electrophoretic bands of both the wild-type and mutant were located at the same position, consistent with the theoretical molecular weight of 35.8 kDa.

Example 4

Enzyme Activity Measurement

20 μL of purified enzyme was mixed with 180 μL of substrate solution (10 mM PLP, 2.5 mM (R)-α-methylbenzylamine, 2.5 mM pyruvate, 30% DMSO, 100 mM PBS, pH 7.5) and reacted at 40° C. for 3 minutes to measure the production of acetophenone at $OD_{245}$. Enzyme activity (U) was defined as the amount of enzyme required to catalyze the transamination reaction of pyruvate and (R)-α-methylbenzylamine to produce 1 μmol of acetophenone per minute under certain conditions.

Figure 3:
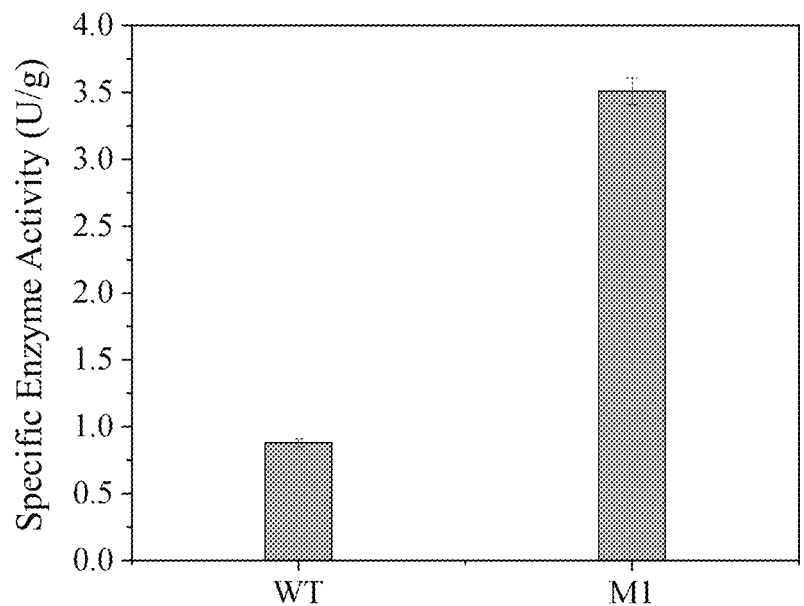
FIG. 3 shows the activity test results of the wild-type D-amino acid transaminase and its mutant in Example 4 of the present invention. The mutant enzyme contains 16 mutation sites (N23P, E35P, Y36P, V37P, E41P, K88P, V89P, E95P, M189P, A192P, Y199P, V232P, E255P, V288P, Q292P, W301P).

The enzyme activity of the wild-type and mutant were shown in FIG. 3, compared to the wild-type, the enzyme activity of the mutant significantly increased, being 4.0 times that of the wild-type.

Example 5

Residual Enzyme Activity Measurement

Figure 4:
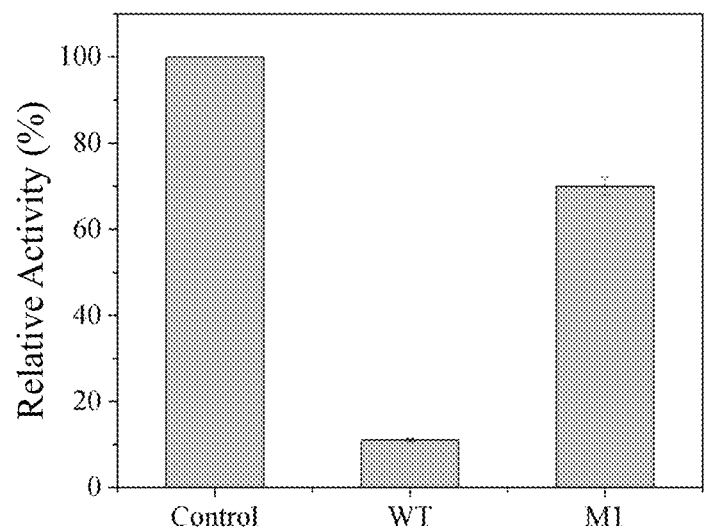
FIG. 4 shows the residual activity of the wild-type D-amino acid transaminase and its mutant after incubating for 10 minutes at 40° C. in Example 5 of the present invention.

The purified wild-type and mutant were incubated at 40° C. for 10 minutes, and then immediately cooled on ice for 10 minutes. Afterwards, 20 μL of heat-treated enzyme solution was mixed with 180 μL of substrate solution (10 mM PLP, 2.5 mM (R)-α-methylbenzylamine, 2.5 mM pyruvate, 30% DMSO, 100 mM PBS, pH 7.5) and reacted at 40° C. for 3 minutes to measure the residual activity of the wild-type and mutant. Taking the enzyme activity of samples not incubated at 40° C. as 100%, the relative activity of the mutant, which was higher than the wild-type, was measured after heat treatment. After a 10-minute heat treatment at 40° C., the residual activities of the wild-type and the mutant were shown in FIG. 4. The activity of the mutant decreased by 30%, while the activity of the wild-type decreased by about 90%.

Example 6

Determination of Enzyme Kinetic Parameters

Substrate solutions of pyruvate at different concentrations (0, 0.1, 0.2, 0.3, 0.5, 1.0, 1.5, 2.0, 2.5, and 3.0 mM) were prepared using PBS buffer (100 mM, pH 7.5) containing 10 mM PLP. The enzyme activities of D-ATA wild-type and mutants at different concentrations were determined using the method for measuring enzyme activity. The reaction rates V at different substrate concentrations [S] for various substrates were inserted into the Michaelis-Menten equation $V = V_{max} \times [S]/(K_m + [S])$, and the kinetic parameters $K_m$ and $V_{max}$ for the wild-type and mutant were calculated using non-linear fitting with Origin 8.0 software. The turnover number $k_{cat}$ and catalytic efficiency $k_{cat}/K_m$ for both the wild-type and mutant were calculated using the formula $k_{cat} = V_{max}/[E]$, wherein [E] was the molar concentration of the enzyme. The results were shown in Table 1. The mutant enzyme M1 showed an increased turnover number for pyruvate and a decreased $K_m$ value compared to the WT, indicating enhanced affinity.

TABLE 1

Kinetic parameters of wild-type and mutant

| Name | $k_{cat}^{pyruvate}$ ($s^{-1}$) | $K_m^{pyruvate}$ (mM) | $k_{cat}/K_m^{pyruvate}$ (L/(s · mmol)) |
|---|---|---|---|
| WT | 0.40 ± 0.01 | 0.35 ± 0.03 | 1.14 |
| M1 | 1.70 ± 0.02 | 0.22 ± 0.02 | 7.73 |

Example 7

Determination of $T_{50}^{15}$ $T_{50}^{15}$ refers to the temperature at which the residual activity of the pure enzyme decreases to 50% after incubation between 4-60° C. for 15 minutes. The purified wild-type enzyme and its mutant were incubated at temperatures of 4° C., 25° C., 30° C., 35° C., 40° C., 45° C., 47° C., 49° C., 50° C. and 55° C. for 10 minutes, rapidly cooled on ice for 5 minutes, and the residual activities of wild-type and its mutant were measured. Using temperature as the x-axis and the ratio of heat-treated to non-heat-treated enzyme activity as the y-axis, graphs were plotted using Origin 8.0 software, and the $T_{50}^{15}$ for the wild-type and mutant were calculated.

Example 8

Determination of $t_{1/2}$ $t_{1/2}$ refers to the time at which the residual activity of the pure enzyme decreases to 50% after incubation at 40° C. for various durations. The purified wild-type and its mutant were incubated at 40° C. for 0 to 24 hours, rapidly cooled on ice for 5 minutes, and the residual activities of wild-type and its mutant were measured. Using time as the x-axis and the ratio of heat-treated to non-heat-treated enzyme activity as the y-axis, graphs were plotted using Origin 8.0 software, and the $t_{1/2}$ at 40° C. for the wild-type and mutant were calculated.

The results of the supercomputing-assisted stability determination for WT and M1 were shown in Table 2. The $T_{50}^{15}$ for the wild-type was 39.9° C., while for the mutant, it was 45.3° C., indicating a 5.4° C. increase compared to the wild-type. The $t_{1/2}$ for the mutant was greater than 12 hours (780.3 minutes), compared to only 8.8 minutes for the wild-type, showing an 87.7-fold increase in half-life for the mutant compared to the wild enzyme.

TABLE 2

Stability parameters of wild-type and mutants

| Name | $T_{50}^{15}$ (° C.) | $t_{1/2}$ (min) |
|---|---|---|
| WT | 39.9 ± 0.4 | 8.8 ± 0.2 |
| M1 | 45.3 ± 0.6 | 780.3 ± 2.2 |

Example 9

Figure 5:
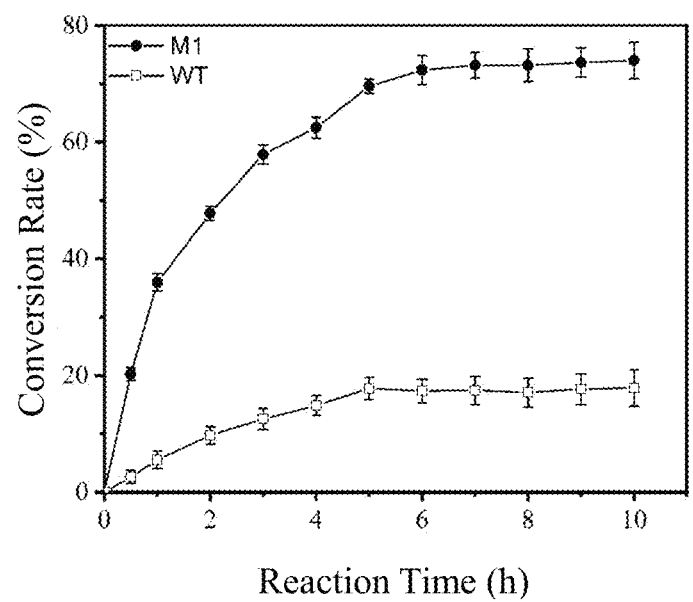
FIG. 5 shows the reaction process for the catalysis of 20 mM pyruvate to D-alanine by the wild-type D-amino acid transaminase and its mutant in Example 9 of the present invention.

The Reaction Process of WT and Mutant M1 in Catalyzing the Conversion of 20 mM Pyruvate to D-Alanine In a 20 mL reaction system, 1.0 g/L of purified enzyme solution, 20 mM pyruvate, 20 mM (R)-α-methylbenzylamine, 20 mM PLP, 30% (v v) DMSO, and 100 mM PBS buffer at pH 7.5 were mixed. The mixture was stirred at 40° C., 600 rpm, and samples were taken periodically to determine the conversion rate. The results, as shown in FIG. 5, indicated that the catalytic efficiency of mutant M1 was significantly higher than that of WT.

It should be noted that the above descriptions are only preferred embodiments of the present invention and are not intended to limit the present invention. Although the present invention has been described in detail with reference to these embodiments, it will be understood by those skilled in the art that they can make modifications or equivalent substitutions to the technical solutions described in these embodiments. Any modification, equivalent replacement, or improvement made within the spirit and principles of the present invention should be included within the scope of the present invention's protection. Although specific embodiments of the present invention have been described herein, this description is not intended to limit the scope of the present invention. Those skilled in the art should understand that various modifications or variations that can be made by those skilled in the art without departing from the spirit and scope of the present invention are still within the protection scope of the present invention.

What is claimed is:

1. A mutant of D-amino acid transaminase, comprising mutations at 16 amino acid sites of a wild-type D-amino acid transaminase, the mutations comprise: N23P, E35P, Y36P, V37P, E41P, K88P, V89P, E95P, M189P, A192P, Y199P, V232P, E255P, V288P, Q292P, W301P, the NCBI accession number of the wild-type D-amino acid transaminase is XP_031942666.1.

2. A polynucleotide molecule encoding the mutant of D-amino acid transaminase as claimed in claim 1.

3. A recombinant expression vector comprising a polynucleotide molecule as claimed in claim 2.

4. A host cell comprising a recombinant expression vector as claimed in claim 3.

5. A host cell expressing the mutant of D-amino acid transaminase of claim 1.

6. The host cell as claimed in claim 4, wherein the host cell is a prokaryotic cell or a eukaryotic cell.

7. A method for fermenting the mutant of D-amino acid transaminase as claimed in claim 1, comprising culturing a host cell that includes a recombinant expression vector comprising a polynucleotide molecule encoding the mutant of D-amino acid transaminase, and isolating the mutant of D-amino acid transaminase.

8. A host cell having a polynucleotide molecule as claimed in claim 2 chromosomally integrated.

* * * * *